United States Patent [19]

Strässle et al.

[11] 4,271,122
[45] Jun. 2, 1981

[54] CONTROL PLASMA

[75] Inventors: Rudolf Strässle, Riehen; Hans Zaugg, Frenkendorf, both of Switzerland

[73] Assignee: Hoffmann-La Roche Inc., Nutley, N.J.

[21] Appl. No.: 31,657

[22] Filed: Apr. 19, 1979

[30] Foreign Application Priority Data

Apr. 27, 1978 [CH] Switzerland .......................... 4582/78

[51] Int. Cl.³ ........................ C09K 3/00; G01N 33/48
[52] U.S. Cl. .................................... 422/61; 23/230 B; 23/918; 252/408; 435/13; 424/3; 424/101; 424/281; 424/283
[58] Field of Search .................... 435/13; 252/408; 23/230 B, 918; 424/101, 3, 281, 283, 183; 422/61

[56] References Cited

U.S. PATENT DOCUMENTS

| 2,281,989 | 5/1942 | Parfentjev | 424/101 |
|---|---|---|---|
| 2,543,674 | 2/1951 | Swayne et al. | 424/281 |
| 2,872,457 | 2/1959 | Schroeder et al. | 424/281 |
| 2,999,049 | 9/1951 | Link | 424/281 |
| 3,325,515 | 6/1967 | Schmitt et al. | 424/281 |
| 3,486,981 | 12/1969 | Speck | 252/408 |
| 3,957,824 | 5/1976 | Hadler et al. | 424/281 |
| 4,007,008 | 2/1977 | Becker et al. | 424/101 |
| 4,056,484 | 11/1977 | Heimburger et al. | 252/408 |
| 4,116,635 | 9/1978 | Jaeger | 424/101 |

FOREIGN PATENT DOCUMENTS

| 107987 | 8/1974 | German Democratic Rep. | 252/408 |
|---|---|---|---|
| 38-2543 | 3/1963 | Japan | 424/101 |
| 906860 | 9/1962 | United Kingdom | 424/101 |

*Primary Examiner*—Teddy S. Gron
*Attorney, Agent, or Firm*—Jon S. Saxe; Bernard S. Leon; James H. Callwood

[57] ABSTRACT

Control plasma of non-human origin to be utilized in the monitoring of oral anticoagulant therapy in human beings, prepared from blood of stable anticoagulated mammals, is described.

15 Claims, No Drawings

CONTROL PLASMA

BRIEF DESCRIPTION OF THE INVENTION

The invention relates to control plasma of non-human origin which is prepared from blood of stable, adjusted and anticoagulated mammals and is utilized to monitor oral anticoagulant therapy in humans.

DETAILED DESCRIPTION OF THE INVENTION

The use of oral anticoagulants, for example, the coumarin derivatives, for thrombosis prophylaxis following surgery or for long term treatment of infarct patients and patients with thrombo-embolic illnesses, must, as is known, be monitored or supervised very closely. In the case of over-dosaging, bleeding can occur, in the case of under-dosaging thrombo-embolic incidents can occur.

For these reasons, it is necessary, therefore, for the protection of the patient, to regularly check whether the doses administered have been correctly chosen. This is effected as a rule by determination of the coagulation time of the plasma (thromboplastin time) of the patient treated utilizing thromboplastin and calcium according to methods which are based on the determination which has been described by Quick, A.J. in The Physiology and Pathology of Hemostasis p. 125, London, Klimpton 1951. After an operation, such monitoring or supervision of the therapy is effected at first every day, then at greater time intervals.

The doses of anticoagulants have been chosen correctly when the obtained Quick value or the thromboplastin time ratio [compare Biggs et al., British Medical Journal (1967) p. 84–88] is in the range of the so-called therapeutic range. This therapeutic range, in which the risk not only of bleeding but also of thromboses is minimal, can be expressed in Quick values (percentage dilution of a mixed plasma from several healthy donors gives the same thromboplastin time as the plasma sample to be tested), or in thromboplastin time ratios (ratio of the thromboplastin time of the patient's plasma to be tested to the thromboplastin time of a mixed plasma from several healthy donors treated in the same manner). Not only the Quick value, but also the thromboplastin time ratio are dependent on thromboplastin employed. As a rule, however, the therapeutic range lies approximately at a Quick value in the range of from 10 to 35% or a thromboplastin time ratio between 1.5 and 5.0. It has, however, been proved that the accuracy and precision of the determination of the Quick values or the thromboplastin time ratios must be controlled not only by use of a normal control plasma (Quick value in the range of from 70 to 100%; thromboplastin time quotient 1.15–1) but also a control plasma with a Quick value or a thromboplastin time ratio in the therapeutic range (denoted hereinafter as pathological control plasma).

Until now, pathological control plasmas have been prepared for the most part by adsorption of various coagulation factors, especially the factors II, VII, IX and X. In a preferred process, human plasma is stirred with aluminum hydroxide and the mixture is centrifuged. The sediment contains the coagulation factors to be removed and the supernatant yields, after possible mixing with normal non-adsorbed plasma, pathological control plasma with a Quick value or a thromboplastin time ratio in the therapeutic range.

The pathological control plasmas which have been prepared in this manner, are however, not entirely satisfactory, because their composition differs very substantially indeed from that of the patient's plasma. In particular, in such a control plasma there are missing the PIVKA factors (PIVKA = Protein Induced by Vitamin K Absence or Antagonists.) These PIVKA factors, which are obtained from different thromboplastin reagents of differing sensitivity, have a substantial influence on the measured Quick value or on the thromboplastin time quotient and should therefore be present in the pathological control plasma in order to guarantee a reliable control in the therapeutic range.

As a consequence of the disadvantage of the pathological control plasmas prepared by adsorption, there has been employed, to some extent overlooking this, the control plasma from stable adjusted orally anticoagulated liver-healthy patients. One such control plasma, which exhibits a Quick value or a thromboplastin time ratio in the therapeutic range, and, among other things, contains the important PIVKA factors, has a composition corresponding largely to the patient's plasma and whereby, therefore, enables the particularly complex and disturbance-susceptible thromboplastin time determination to be assured by an efficient quality control. A substantial disadvantage is, however, that the starting material for the preparation of such anticoagulated pathological control plasmas comprises the rest of the patient's plasma samples as obtained in clinical laboratories. This is circumstantially so, because the plasma samples of anticoagulated patients are collected daily from different hospitals and must be stored deep-frozen. In contrast to normal blood donors, which in the healthy state donate their blood voluntarily, in the foregoing test there is employed the blood taken in excess from ill human patients. This method may be usable and operable on a small scale, but in no way can be utilized by the entire diagnostic industry not only on ethical but also on technical and logistic grounds.

It has now been found that by anticoagulation in mammals, especially in sheep, there can be prepared a pathological control plasma with a Quick value and a thromboplastin time ratio in the therapeutic range, which exhibits a composition analogous to the patient's plasma and, among other things, contains the important PIVKA factors. The pathological control plasma in accordance with the invention guarantees the same quality of the control as the anticoagulated pathological control plasma of patients, without exhibiting the disadvantages described in the previous paragraphs.

More specifically, the present invention relates to a control plasma of non-human origin for the supervision or monitoring of oral anticoagulant therapy in humans, prepared from blood of stable, adjusted and anticoagulated mammals.

It has been found that this control plasma differs only relatively little from control plasma from stable anticoagulated humans and corresponds to the control plasma of stable anticoagulated patients especially in functional respects. The essential difference, namely, the higher factor V activity (ratio of the factor V activity to that of a human plasma greater than 2, preferably between 2 and 5) of the control plasma in accordance with the invention, has no influence on its quality for the control of the thromboplastin time determination.

The control plasma of the invention can be prepared in mammals treated with an anticoagulant, and adjusted to a value in the therapeutic range by means of supervision or monitoring of Quick value or thromboplastin time ratio. The plasma, after blood withdrawal from such mammals into an agent which prevents the spontaneous blood coagulation, is produced by centrifugation and a buffer is added to the obtained plasma for the purpose of adjusting a physiological pH-value.

Mammals which are especially suitable for the purpose of the present invention are cows, horses, goats, rabbits, pigs, dogs and sheep. Sheep are especially preferred.

The type of anticoagulant utilized is not critical. However, there are preferably employed coumarin derivatives such as 3-(1-phenyl-propyl)-4-hydroxy-coumarin (phenprocoumon); 3-(α-[-4-nitrophenyl]-β-acetylethyl)-4-hydroxycoumarin (acenocoumarin); 3-(α-phenyl-β-acetylethyl)-4-hydroxy-coumarin (warfarin sodium); 3,3'-carbethoxymethylene-bis-(4-hydroxy-coumarin) (ethylbiscoumacetable); 3,3'-methylene-bis-(4-hydroxy-coumarin) (bishydroxycoumarin). 3-(1-Phenyl-propyl)-4-hydroxycoumarin is especially preferred.

The treatment can be effected not only orally but also intravenously. An oral treatment is, however, preferred. The method of treatment, especially the dosage employed and the duration of this treatment, depends among other things on the anti-coagulant utilized on the animal species, on the weight and on the sensitivity of the animal. As a rule, however, there are administered to the animal dosages of approximately 0.8 mg/kg, at least daily, for at least a one-month period. The animal preferably always receives feed of the same composition during the entire treatment.

Blood samples are removed periodically, preferably about 2 times weekly, by venous puncture for the supervision or monitoring of the thromboplastin time ratio or the Quick value.

To prepare the desired control plasma, after stable adjustment of the Quick value or thromboplastin time quotient in the therapeutic range, blood is removed, preferably by venous puncture, over a period of more than two weeks in appropriate time intervals (in the case of sheep at most every two weeks) in the presence of an agent for the prevention of the spontaneous blood coagulation. As agent for the prevention of the spontaneous blood coagulation there are suitable complex formers for calcium ions, such as, for example, trisodium citrate, ethylenediaminetetraacetic acid (EDTA) or sodium oxalate. These complex formers are employed in amounts and concentrations which are usual in the blood withdrawal in the case of humans. Thus, trisodium citrate is preferably employed in the form of a 0.1 molar solution in a ratio of 1 to 9 to the blood to be removed.

Plasma is obtained from the blood sample in the usual manner by centrifugation. Advantageously, to prepare the desired control plasma several plasma portions obtained in this way can be mixed.

For the stabilization of the control plasma at a physiological pH-value of 7.2 to 7.5 there is preferably added a suitable buffer, such as, for example, Tris buffer, phosphate buffer, imidazole buffer, or N-2-hydroxyethylpiperazine-N'-ethanesulfonic acid (HEPES).

In order to guarantee that in the plasma the thrombocytes are largely removed, the plasma is preferably centrifuged and sediment which may still be present is removed.

The control plasma of the invention can be maintained in liquid, frozen or lyophilized condition. Preferably, it is stored in lyophilized form or is packed in reagent packs for the control of the thromboplastin time.

One such reagent pack can additionally contain in additional containers the thromboplastin reagent, and/or the normal control plasma and/or a solution for the prevention of the spontaneous blood coagulation.

The invention is more precisely illustrated on the basis of the following Example.

EXAMPLE

Oral anticoagulation of sheep

Ten sheep (female, not pregnant, average weight about 50 kg.) are presented as a group. The animals are characterized by earmarks and for each animal there is prepared a protocol sheet on which the animal weight before beginning of the treatment as well as all manipulations during the duration of the treatment are registered. Regarding the feed composition, this is not altered during the duration of the treatment. Phenprocoumon capsules [20 mg. of 3-(1-phenyl-propyl)-4-hydroxy-coumarin in an interlocking gelatin capsule] are administered to each animal through an oesophageal tube and indeed in the morning and possibly in the evening. The dosage is effected individually for each animal. During the first four days, the animals are usually given decreasing doses, e.g. 4 capsules the first day, 3 capsules the second, 2 capsules the third and 1 capsule the fourth day. The further dosage is effected individually according to the Quick value found. This has given e.g. the following dosage scheme for an animal:

| Treatment day | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|---|---|---|---|
| Number of capsules per day | 4 | 3 | 2 | 1 | 2 | 2 | 1 | 2 | 2 | 1 | 2 | 2 | 1 | 2 | 2 | 1 | 2 | 2 | 1 | 2 | 2 | 1 | 2 | 2 | 2 | 1 | 2 | 2 | 1 |

The control blood withdrawals for the Quick value determination are carried out in each case before the daily phenprocoumon dose by adding 9 ml. of blood/animal to 1 ml. of 0.1-M tri-sodium citrate with a syringe. The Quick value determination with plasma is effected first of all daily, then weekly 1-2 times. After about 30 days from the beginning of the treatment, the animals are adjusted within the therapeutic range.

MANUFACTURE OF PATHOLOGICAL CONTROL PLASMA

40 Ml. of 0.1-M sodium citrate solution are added to blood donation flasks 500 ml, siliconized. By venous puncture (V. jugularis) the blood of the sheep treated with phenprocoumon is then allowed to flow into the flask up to the 400 ml. mark. During this time, a good intermixing is provided for by slight agitations of the flask constantly. The collected blood is then further processed to plasma as rapidly as possible. The centrifugation is effected at 2500 r/min. (about 1600 xg) and 10° C. during 30 minutes. The plasma is carefully sucked off with a siliconized pipette and propipette and added to a 250 ml. plastic beaker. The thromboplastin time (TPT) of the individual plasmas is determined and then each 200 ml. of individual plasma is pooled on the basis of the Quick value. The found Quick value range of the plasma pool amounts to 20–25% for rabbit lung calcium-thromboplastin. The addition of solid N-2-hydroxyethylpiperazine-N'-ethanesulfonic acid (HEPES) is effected up to the concentration of 0.05-M (11.9 g. of HEPES/100 ml. of plasma). After centrifugation (15 minutes; 700 xg) at 10° C. in plastic beakers, the supernatant plasma is carefully decanted off and filled as rapidly as possible in 0.5 ml. aliquots into ampul flasks and lyophilized.

PROPERTIES (a) Quick value and thromboplastin time ratio

The ampul content is dissolved in the corresponding volumes of distilled water. The solution is left to stand at 37° C. for 5 minutes, then at room temperature for 10 minutes and the thromboplastin time determination (TPT) is carried out with rabbit lung calcium-thromboplastin.

| Batch | rabbit lung calcium-thromboplastin Quick value | Thromboplastin time ratio |
|---|---|---|
| 1 | 25% | 1.78 |
| 2 | 24.5% | 1.81 |
| Stable anticoagulated human plasma | 24% | 1.7 |

FACTOR CONTENT

The coagulation factors II, V, VII/X and X were determined according to the method of Marbet and Winterstein (J. Jürgens/F. K. Beller Clinical Methods of Blood Coagulation Analysis, Thieme-Verlag 1959). The data in % of the standard relate to human citrate plasma.

The fibrinogen content was determined according to the method of Blomback [Blomback, Arkiv. Kemi. 10, 415–422 (1956)] [with modification of Jacobson, Scand. J. Clin. and Lab. Invest. Suppl. 14 (1955), 1–102.]

| Batch | Fibrinogen mg % | Factor content in % relative to normal human plasma | | | |
|---|---|---|---|---|---|
| | | II | V | VII/X | X |
| 1 | 387 | 6.9 | 335 | 9 | 16 |
| 2 | 355 | 7.3 | 300 | 11 | 20.5 |
| Stable anticoagulated human plasma | 300 | 10.5 | 115 | 15.5 | 13.9 |

We claim:

1. A process for the preparation of a control plasma for monitoring oral anti-coagulant therapy in humans, characterized in that mammals are treated with an anti-coagulant selected from the group consisting of coumarin and coumarin derivatives until the blood plasma of said mammals is, adjusted to and stabilized at a value in the therapeutic range by means of monitoring the Quick value or thromboplastin time ratio, and, thereafter, the blood is withdrawn into an agent which prevents spontaneous blood coagulation, the plasma obtained by centrifugation, and a buffer is added to theobtained plasma to adjust the plasma to a physiological pH-value.

2. A process, in accordance with claim 1, characterized in that sheep are employed as the mammals.

3. A process, in accordance with claim 2, characterized in that the agent for the prevention of the spontaneous blood coagulation is trisodium citrate.

4. A process, in accordance with claim 3, characterized in that the buffer for the adjustment of the physiological pH-value is N-2-hydroxyethylpiperazine-N'-ethanesulfonic acid.

5. A process, in accordance with claim 4, characterized in that after addition of the buffer the plasma is again centrifuged.

6. A process, in accordance with claim 5, characterized in that the obtained control plasma is lyophilized.

7. Control plasma of non-human origin having a Quick value in the range of from 10 to 35 percent for the monitoring of oral anticoagulant therapy in humans prepared by treating mammals with an anti-coagulant selected from the group consisting of coumarin and coumarin derivatives until the blood plasma of said mammals is adjusted to and stabilized at a value in the therapeutic range by means of monitoring the Quick value or thromboplastin time ratio, and, thereafter, withdrawing the blood into an agent which prevents spontaneous blood coagulation, obtaining the plasma by centrifugation, and adding a buffer to the obtained plasma to adjust the plasma to a physiological pH-valve.

8. Control plasma, in accordance with claim 1, wherein said control plasma is prepared from blood of sheep.

9. Control plasma, in accordance with claim 8, characterized in that the ratio of its factor V activity to that of a human plasma is greater than 2.

10. Control plasma, in accordance with claim 9, characterized in that the ratio of its factor V activity to that of a human plasma is 2 to 5.

11. Control plasma, in accordance with claim 1, wherein the agent which prevents spontaneous blood coagulation is trisodium citrate.

12. Control plasma, in accordance with claim 11, wherein the buffer is N-2-hydroxyethylpiperazine-N'-ethanesulfonic acid.

13. Lyophilized control plasma prepared according to the method of claim 6.

14. A reagent pack for the monitoring of anticoagulant therapy in humans which comprises a container of a control plasma having a Quick value in the range of 10 to 35 percent of non-human origin for the monitoring of oral anticoagulant therapy in humans prepared according to the method of claim 1.

15. A reagent pack for the monitoring of anticoagulant therapy in humans which comprises:
  (a) in a first container a control plasma of non-human origin for the monitoring of oral anticoagulant therapy in humans prepared according to the method of claim 10;
  (b) in a second container a normal human control plasma;
  (c) in a third container a thromboplastin reagent; and
  (d) in a fourth container an agent for the prevention of the spontaneous blood coagulation.

* * * * *